United States Patent [19]

Antoniades

[11] 4,194,056
[45] Mar. 18, 1980

[54] ACETIC ACID FROM METHYL FORMATE

[75] Inventor: Emilios P. Antoniades, El Cerrito, Calif.

[73] Assignee: Chevron Research Company, San Francisco, Calif.

[21] Appl. No.: 77,328

[22] Filed: Sep. 30, 1970

[51] Int. Cl.$^2$ ............................................. C07C 51/10
[52] U.S. Cl. ................................................... 562/516
[58] Field of Search ................ 260/541, 540; 562/517

[56] References Cited
U.S. PATENT DOCUMENTS 3,839,428  10/1974  Isogai ................................. 260/541

FOREIGN PATENT DOCUMENTS 713295  4/1968  Belgium ................................. 260/532

Primary Examiner—Robert Gerstl
Attorney, Agent, or Firm—D. A. Newell; John Stoner, Jr.

[57] ABSTRACT

Acetic acid is obtained by heating methyl formate in the presence of soluble rhodium salt catalyst and halogen promoter and sufficient carbon monoxide to convert said rhodium salt into at least a monocarbonyl compound.

5 Claims, No Drawings

ACETIC ACID FROM METHYL FORMATE

BACKGROUND OF INVENTION

1. Field of Invention

This invention relates to the preparation of acetic acid from methyl formate. More particularly, the invention is concerned with a rhodium catalyzed, halogen promoted rearrangement of methyl formate into acetic acid.

2. Prior Art

The direct conversion of methyl formate into acetic acid is already known. U.S. Pat. No. 2,508,513 claims a liquid-phase process for making acetic acid by heating methyl formate in the presence of a carbonyl-forming metal catalyst and a halogen. The catalysts are further defined as one or more of the iron metals, preferably nickel. Other metals of less activity are tungsten, vanadium, antimony, and bismuth. The process of this patent is a high temperature, above 300° C., process. Carbon monoxide is advantageous to the process. No yields are reported; but the reaction product contains acetic acid, methyl acetate, and some formic acid.

Another patent, U.S. Pat. No. 1,697,109, claims the vapor-phase isomerization of methyl formate into acetic acid by heating it in the presence of a catalyst. The catalysts are either (1) metal acetates which decompose with the formation of acetic acid at a temperature under 450° C. or (2) a metal compound capable of forming said acetates. Typical catalysts are salts of copper, tin, lead, zinc, and aluminum. The reaction is carried out at temperatures in the range of 100°–450° C., preferably 200°–300° C. No examples are given.

SUMMARY OF THE INVENTION

A new process has now been discovered for the preparation of acetic acid which comprises heating methyl formate in the presence of soluble rhodium salt catalyst, halogen promoter and sufficient quantity and pressure of carbon monoxide to convert said rhodium salt into at least a monocarbonyl compound, said heating being carried out at temperatures within the range of from about 150° to about 350° C.

The present invention process results in yields of acetic acid in excess of 95%. The conversion of methyl formate is essentially 100%.

DETAILED DESCRIPTION OF THE INVENTION

The rhodium catalyst is employed in the form of any rhodium salt capable of supplying rhodium ion—for example, tris(triphenylphosphine) chlororhodium (I), chlorocarbonyl bis(triphenylphosphine) rhodium, rhodium trichloride, etc. The preferred catalyst is tris(triphenylphosphine) chlororhodium (I). These catalysts are known compounds and have been used to catalyze the carbonylation of methanol to acetic acid (Ref. J. Catalysis, January 1969, page 105). Catalyst concentrations are in the range of 0.0001 to 0.01, preferably 0.001 to 0.005 mol of rhodium per liter of methyl formate. Higher concentrations of catalysts are recommended for low temperature reactions.

The halogen promoter for this reaction may be iodine, hydrogen iodide, methyl iodide, calcium iodide, etc. Methyl iodide is preferred. Under constant reaction conditions, the rate of reaction is increased with increased concentration of promoter. In general, promoter concentrations range from 0.1% to 50%, preferably 5% to 25% by weight based on methyl formate. At least one mol, preferably 2 mols, of promoter per mol of rhodium should be employed.

Under the usual conditions of the reaction, satisfactory conversions may be reached in as little as 1 to 5 minutes, or as long as 24 hours. Short reaction times are favored by high temperatures, high catalyst concentrations, and/or high promoter: catalyst ratios. The reaction may be carried out in the presence of solvents, such as benzene, acetic acid, etc. However, it is preferred to carry out the reaction neat, i.e., without solvents.

Carbon monoxide must also be present in this reaction in sufficient quantity and pressure to convert the rhodium salt into at least a monocarbonyl compound. Therefore, it is desirable to use in excess of one mol of carbon monoxide per mol of rhodium in at least some measurable pressure. As a practical matter, initial carbon monoxide pressures in excess of 20 psi are used. Initial pressures as high as 500 psi have been used. It is preferred that the initial carbon monoxide pressure be in the range of 200–500 psi. Pressure during reaction is much higher, depending on the temperature employed. However, the pressure remains essentially constant throughout a batch run, indicating that carbon monoxide is not consumed during the formation of acetic acid. A relatively high pressure of carbon monoxide is desirable in order to prevent catalyst decomposition.

The following metal salts were not catalysts for this reaction, at temperatures in the range of 170°–200° C.: cobalt iodide, cobalt iodide/triphenylphosphine, nickel iodide, copper chloride/triphenylphosphine, ferrous chloride/triphenylphosphine, tungsten hexacarbonyl, rhenium pentacarbonyl, and molybdenum hexacarbonyl. Rhodium was the only satisfactory catalyst.

The preferred method of operation involves continuously charging to a plug-flow tubular reactor, a carbon monoxide saturated methyl formate solution containing 0.04 mol of tris(triphenylphosphine) chlororhodium (I) and 1.25 mols of methyl iodide per liter. The reactor is held at 350° C.; and the rate of feed is such as to give 100% conversion, i.e., a residence time of about 2 minutes.

The following examples illustrate the process according to the present invention. These examples are in no manner intended to limit the invention described. Unless otherwise indicated, percentages are on a weight basis.

EXAMPLE 1

Preparation of Acetic Acid

A small stainless steel tube, having a capacity of 16 ml, was charged with 6.0 grams (0.1 mol) of methyl formate (MF), 0.1 gram of tris(triphenylphosphine) chlororhodium (I), and 0.224 gram of methyl iodide (MI). The vapor space was purged three times by pressuring up to 500 psi with carbon monoxide and then carefully venting. The tube was then pressured to 500 psi with carbon monoxide and sealed. The tube was placed in a large metal heating block previously heated to 170° C. The heating block and enclosed tube were then shaken at 30 cycles per minute for 16 hours.

At the end of this time, the tube was quenched by placing it in cold water. The tube was opened and vented. The liquid contents, weighing 5.2 grams, were analyzed by vapor-phase chromatography. The reaction product had the following composition: 99.1% acetic acid (AA), 0.1% methyl formate (MF), and 0.4% methyl acetate (MA).

Other reactions were carried out using the same equipment and the same general procedure but with varying reaction conditions. The conditions and results of these runs are given in the following table.

TABLE

| Ex. No. | Catalyst[1] Type | Catalyst[1] Grams | MF, Grams | MI, Grams | $CO^2$ psig | Temperature, °C. | Time, Hr. | Liquid Product Distribution, Wt. % MF | Liquid Product Distribution, Wt. % AA | Liquid Product Distribution, Wt. % MA |
|---|---|---|---|---|---|---|---|---|---|---|
| 2 | A | 0.1 | 6.0 | 0.224 | 500 | 170 | 4 | 39 | 50 | 6 |
| 3 | A | 0.1 | 6.0 | 0.224 | 500 | 200 | 2 | 25 | 62 | 8 |
| 4 | C | 0.022 | 6.0 | 0.224 | 500 | 200 | 2 | 65 | 24 | 6 |
| 5 | B | 0.1 | 6.0 | 0.224 | 500 | 200 | 2 | 44 | 44 | 6.1 |
| 6 | A | 0.1 | 6.0 | 0.224 | 400 | 200 | 2.2 | 5 | 90 | 4 |
| 7 | A | 0.1 | 6.0 | 0.224 | 200 | 200 | 2 | 1.6 | 95 | 1.5 |
| 8 | A | 0.1 | 6.0 | 0.224 | 100 | 200 | 2 | 2.9 | 91 | 3.4 |
| 9 | A | 0.1 | 6.0 | 0.224 | 50 | 200 | 2 | 11 | 63 | 16 |
| 10 | A | 0.1 | 6.0 | 0.224 | 25 | 200 | 1.75 | 47 | 26 | 19 |
| 11 | A | 0.1 | 6.0 | 0.224 | 500 | 250 | 0.5 | 0.0 | 98 | 0.2 |
| 12 | A | 0.02 | 3.0[3] | 0.224 | 500 | 300 | 0.25 | 0.0 | 96 | 0.9 |
| 13 | A | 0.1 | 3.0[4] | 0.224 | 500 | 300 | 0.16 | 0.3 | 93 | 3.1 |
| 14 | A | 0.2 | 6.0 | 0.224 | 200 | 200 | 1.0 | 52 | 34 | 10.3 |
| 15 | A | 0.1 | 6.0 | 1.120 | 200 | 200 | 0.5 | 43 | 44 | 1.5 |
| 16 | A | 0.45 | 6.0 | 1.0 | 200 | 200 | 0.5 | 4.3 | 91 | 0.5 |
| 17[5] | A | 0.1 | 12.0 | 0.224 | 200 | 200 | 2.0 | 21 | 59[6] | 10.1 |
| 18 | A | 0.1 | 6.0 | 0.224 | 200[7] | 200 | 2.0 | 33 | 54 | 6 |

[1]Catalyst A = tris(triphenylphosphine)chlororhodium (I). Catalyst B = chlorocarbonyl bis(triphenylphosphine) rhodium (I). Catalyst C = rhodium trichloride.
[2]Carbon monoxide pressure measured at ambient temperature.
[3]Run included 3.0 ml of acetic acid.
[4]Run included 3.0 ml of paraxylene.
[5]Mixture not shaken during reaction.
[6]Product also had 7.1% formic acid.
[7]Plus 300 psig of hydrogen; total pressure 500 psig.

Example 2, compared with Example 1, shows a decrease in conversion upon shortening reaction time. Examples 3 and 11, compared to Examples 1 and 2, show increased conversion upon simultaneous increasing temperature and reducing reaction time. Examples 4 and 5 are catalyzed by other rhodium salts. Examples 6, 7, 8, 9 and 10 show the effect of changes in initial carbon monoxide pressure. Examples 12 and 13 show good conversions and yields in the presence of solvents. Examples 14, 15 and 16 show the effect of changing catalyst concentration or promoter concentration, or both. Example 17 shows good yields in same reactor with one-half the vapor space as in the previous examples and with no shaking during reaction. In example 18, sufficient hydrogen was added to give a carbon monoxide-hydrogen ratio similar to that of water gas.

The acetic acid produced by this process is easily purified by distillation. It has the same uses as are well known in the art for acetic acid, e.g., solvent, acetylating agent, intermediate, etc.

While the character of this invention has been described in detail with numerous examples, this has been done by way of illustration only and without limitation of the invention. It will be apparent to those skilled in the art that modifications and variations of the illustrative examples may be made in the practice of the invention within the scope of the following claims.

I claim:

1. Process for the preparation of acetic acid which comprises heating methyl formate in the presence of carbon monoxide, a catalytic amount of a soluble rhodium salt carbonylation catalyst, and an iodine-containing promoter, said heating being carried out at temperatures within the range of from about 150° to 350° C. at pressures in excess of 20 psi and with an excess of one mol of carbon monoxide per mol of said rhodium salt.

2. The process of claim 1 in which the halogen promoter is methyl iodide.

3. The process of claim 1 in which the rhodium salt is tris(triphenylphosphine) chlororhodium.

4. The process of claim 1 in which the catalyst concentration is in the range of about 0.0001 to about 0.01 mol of rhodium per liter of methyl formate.

5. A process which comprises converting methyl formate into acetic acid at a temperature of from 150°–350° and in the presence of CO under a pressure of at least 20 psi in presence of a catalyst wherein the catalyst is a combination of (A) a soluble rhodium salt catalyst and (B) an iodine-containing promoter said catalyst being present in an amount 0.0001–0.01 mol of rhodium per liter of methyl formate.

* * * * *